United States Patent [19]

Zivin

[11] Patent Number: 4,898,869

[45] Date of Patent: Feb. 6, 1990

[54] REDUCTION OF STROKE DAMAGE

[76] Inventor: Justin A. Zivin, 31 Camp St., Paxton, Mass. 01612

[21] Appl. No.: 216,084

[22] Filed: Jul. 7, 1988

Related U.S. Application Data

[60] Continuation of Ser. No. 20,558, Mar. 2, 1987, abandoned, which is a continuation of Ser. No. 746,042, Jun. 18, 1985, abandoned, which is a division of Ser. No. 651,501, Jun. 18, 1984, Pat. No. 4,524,072.

[51] Int. Cl.⁴ .............................................. A61K 31/44
[52] U.S. Cl. .................................................. 514/280
[58] Field of Search ......................................... 514/280

*Primary Examiner*—Stanley J. Friedman
*Attorney, Agent, or Firm*—Fish & Richardson

[57] ABSTRACT

A method of reducing stroke-induced neurological damage in a human patient comprising administering to said human patient an effective amount of a pharmaceutically acceptable neurological-damage-reducing serotonin antagonist.

8 Claims, No Drawings

REDUCTION OF STROKE DAMAGE

BACKGROUND OF THE INVENTION

This invention relates to treatments for stroke.

Stroke is a leading cause of death in the United States. The most common type of stroke, focal central nervous system (CNS) ischemia, is characterized by an acute onset of neurological deficit and is primarily caused by the obstruction of an artery to the CNS.

Changes in the level of tissue serotonin [5-hydroxytryptamine] have been shown in experimental models of cerebral ischemia; Welch et al. (1977) *Stroke* 8, 341–6; Harrison et al. (1979) *Stroke* 10 165–8; Jellinger et al. (1978) *J. Neurol Transmission* 14, 31–44.

Harrison, et al., (1981) *J. Neurol. Neurosurg. Psych.* 44, 140–143 investigated the "possible relevance of serotonin changes to the clinical sequelae of cerebral infarction" by measuring the effects of certain serotonin antagonists on neurologic damage in a gerbil stroke model. Eight serotonin antagonists, (5-hydroxy-1-tryptophan, L-tryptophan in conjunction with pargyline, quipazine, methergoline, methysergide "BW 501C", cyproheptidine, and p-chloro-phenylalanine) were typically administered intravenously at doses ranging from 1 mg/Kg to 150 mg/Kg 1 hr. prior to induced cerebral infarction; p-chloro-phenylalanine was administered 24–48 hrs. after infarction at a dosage of 300 mg/Kg. Harrison et al. says that serotonin "receptor antagonists ... failed to produce a striking change in the prevalence of neurological morbidity".

SUMMARY OF THE INVENTION

In general, the invention features a method of reducing stroke-induced neurological damage in a human patient comprising administering to the patient an effective amount of a pharmaceutically acceptable neurological-damage-reducing serotonin antagonist. In preferred embodiments the neurological-damage-reducing serotonin antagonist is administered no later than 24 hours, more preferably 1 hr., and most preferably 20 minutes following the onset of a stroke; or the neurological-damage-reducing serotonin antagonist is administered prior to the onset of a stroke such that at the time of the stroke there is a sufficient amount of neurological-damage-reducing serotonin antagonist present in the bloodstream of the patient to reduce stroke-induced neurological damage.

Neurological-damage-reducing serotonin antagonists of the invention include cinanserin, 2-bromo-lysergic acid diethylamide cyproheptadine, and Lysergic acid diethylamide (LSD) Neurological-damage-reducing serotonin antagonists of the invention alone or in combination with a pharmaceutically acceptable carrier substance, can be administered intravenously intrathecally, orally, subcutaneously, or nasally.

Administration of neurological-damage-reducing serotonin antagonists according to the invention can provide a significant level of protection against stroke. The protective effect can be achieved by administering the neurological-damage-reducing serotonin antagonist to the patient either before or after the onset of stroke.

Other features and advantages of the invention will be apparent from the following description of the preferred embodiments, and from the claims.

DESCRIPTION OF THE PREFERRED EMBODIMENTS

We turn now to a description of the preferred embodiments.

COMPOUND SELECTION

The compounds of the method of the invention are selected by a two-step process. First, the compounds are identified as serotonin antagonists. As used herein, the term serotonin antagonist means any substance which blocks the action of serotonin, whether by competitively inhibiting it, removing it, or any other means. Preferred means of identifying a serotonin antagonist include in vitro binding assays, in vivo electrophysiological tests, or animal behavioral studies. Most preferably, the substance elicits a positive result in one of the specific tests described in detail below. A positive result is defined herein as a test result which is statistically significant, as compared to an appropriate control compound. A partial list of identified serotonin antagonists is found in Fuller, (1980) *Ann. Rev. Pharmacol. Toxicol.* 20, 111–127, hereby incorporated by reference.

In the second step of the selection process, those compounds identified as serotonin antagonists are then defined functionally as neurological-damage-reducing serotonin antagonist (NDR serotonin antagonists) by their ability to alleviate the negative effects of CNS ischemia in a rabbit stroke model without producing toxic side effects which would preclude their use in treatment.

IDENTIFICATION OF SEROTONIN ANTAGONISTS

In vitro binding assays quantitatively measure the extent to which serotonin is displaced from nervous tissue by a test compound. Peroutka et al., (1979) *Mol. Pharm.* 16, 687–699, hereby incorporated by reference, describes competitive binding assays measuring displacement, in rat cortex brain tissue of [$^3$H] serotonin by, e.g., D-LSD, 2-bromo-LSD, methysergide, cyproheptidine, mianserin, and cinanserin. A test compound shown by competitive binding assay to displace serotonin from binding sites is defined as a serotonin antagonist.

In vivo electrophysiological tests are another means of defining a serotonin antagonist Haigle et al. (1977) *Fed. Proc.* 36 2159–2164 measures the rate of nerve firing with a microelectrode implanted in a living neuron. Serotonin is administered to the neuron alone and in conjunction with a test compound. If the test compound inhibits the effect of serotonin on the rate of nerve firing then the test compound is a serotonin antagonist.

A third method of identifying a serotonin antagonist is to use a bioassay in which an animal behavior, which is increased or caused by serotonin, is inhibited or reduced by the administration of the test compound. Sloviter et al. (1978) *J. Pharmacol Exper. Ther.* 206, 339–347 examines the effects of several pharmacological treatments on the expression of a rat behavioral syndrome attributed to serotonin receptor activity and characterized by simultaneous side-to-side head weaving or head tremor, forepaw padding, and splaying of hindlimbs. Meek et al. (1970) -Eur. J. Pharmacol. 9, 325–332 used the extensor hindlimb reflex to measure CNS serotonin receptor activity and found that the amount of serotonin available for release could be increased by, e.g., administration of nialamide (a monoamine oxidase inhibitor) with or without one of the serotonin precursors 5-hydroxytryptophan or tryptophan. A test compound, administered in conjunction with nialamide, that prevents or reduces the extensor reflex of Meek et al. is a serotonin antagonist.

For the purposes of the invention, a test compound exhibiting a statistically significant level of serotonin antagonism in any of the three types of tests described above is defined as a serotonin antagonist.

Functional Identification of Neurological Damage Reducing Serotonin Antagonists The effectiveness of a compound identified as a serotonin antagonist in reducing the permanent neurological damage caused by a stroke is assessed using the rabbit spinal chord ischemia model described in Zivin et al. (1982) *Arch. Neurol.* 39, 408–412, hereby incorporated by reference.

In this model young adult New Zealand male albino rabbits weighing 2 to 3 kg are maintained in individual cages and allowed food and water ad lib for three to five days before surgery. They are anesthetized with ketamine, 20 mg/kg, and open drop ether. Through a midline abdominal incision the aorta is exposed at the level of the renal arteries. A small diameter plastic line is placed around the aorta just distal to the left (caudal) renal artery. The ends of the line are threaded through a 7-mm diameter plastic button and then a 3.18-mm internal diameter polyvinyl chloride tube to form a snare ligature as described by Crowell et al., (1981) *Neurology* 31, 1295–1302. The incision is closed around the tubing so the free ends are accessible externally. The rabbits are allowed to recover from the anesthesia for at least two hours. It is then possible to establish that the rabbits' sensations and motor activities are normal. The aorta of each animal is then occluded by pulling and clamping the line. Adequacy of this method of vascular occlusion has been established by direct visualization. After a fixed interval, release of the line allows restoration of flow through the aorta.

Control subjects consist of rabbits in which the snare ligature is positioned around the aorta but not pulled tight. After surgery all animals receive daily injections of an antibiotic, and Crede's maneuver is performed twice daily on animals that are incontinent.

The animals are observed continuously while the aorta is occluded and for 30 minutes following release of the ligature. They are then examined at 30-minute intervals for the next three hours and then twice daily for one week after occlusion. The degree of neurological impairment is graded on a three-point scale, as follows:

0-No neurological impairment. Animals ambulate normally, respond normally to noxious stimuli, and have normal bowel and bladder function.

1-Partial neurological deficit. Animals do not hop normally and are less responsive than normal to pinching of the hind limbs. Bowel and bladder function is variable. Animals showing any degree of impairment of these clinical factors (from barely detectable to extremely severe) are included in this grade.

2-Complete neurological impairment. Animals are completely paraplegic, unresponsive to noxious stimuli in the hindquarters, and incontinent of urine and feces.

Most rabbits become paraplegic immediately when the snare ligature is pulled tight. A few maintain sensory or motor functions for several seconds after initiation of occlusion, but all animals become completely paraplegic within two minutes. When the ligature is released, four patterns of response are noted, as follows:

1. Return to normal (grade 0).
2. Incomplete recovery with partial deficits (grade 1) that remain unchanged for the subsequent week.
3. Return to normal or partial deficits initially, and then, between three and 96 hours later, further deficits are noted (grade 1 or 2). We designate this as "the pattern of evolving deficits".
4. Persistence of complete paraplegia (grade 2).

To evaluate quantitatively the relationship between the duration of aortic occlusion and the fraction of animals showing development of neurological dysfunction, logistic curves are fitted to the quantal dose-response data by use of an iterative technique based on a Taylor series expansion described by Waud, (1972) *J. Pharm. Exp. Ther* 183, 577–607. The differences in these curves are tested by a conservative use of group t test.

The method used for the statistical analysis of the data is chosen because the neurological deficits are classified according to a three-point scale (no deficits, partial deficits, or complete paraplegia) as a function of the time of occlusion. Therefore the data are analogous to pharmacologic data where, for example, one is testing the potency of a drug by observing the fraction of groups of animals that are killed by a given dose. In such pharmacologic tests, an animal is either alive or dead, and in our data, an animal either has a neurological deficit, or does not. The dose of drug that results in death of 50% of the animal ($LD_{50}$) is analogous to the duration of ischemia that results in the production of neurological deficits in 50% of the rabbits ($ET_{50}$).

The results can be fitted with a logistic curve. The equation of the logistic function is $P = D^s/(D^s + M^s)$, where P is the probability of a deficit (fraction of a large group of animals that will have the deficit), D is the duration of occlusion, M is the mean time required to produce deficits (50% of a large population of rabbits will show deficits if occluded for this length of time) and S is the "slope" of the logistic curve. S is not a true slope in the usual sense (dy/ox); it is a dimensionless exponent that is a measure of the steepness of the logistic curve. If S is large (i.e., the logistic curve is steep) the length of occlusion that will produce irreversible damage in the most susceptible animals is not much less than the length of occlusion that produces damage in the most resistant animals. Conversely, if S is small, some animals will be damaged after relatively short periods of occlusion, whereas other animals will require relatively long periods of ischemia before permanent damage is produced. Thus, S is a measure of the spread of the data about the length of time of ischemia that produces damage in one half of the animals.

The actual curve fitting process is iterative; initial estimates of M and S are given. Then, these values are systematically refined until they show no further improvement.

In order to determine whether a serotonin antagonist effectively reduces the neurological damage caused by a stroke, the neurologic function in animals treated with a serotonin inhibitor is compared to neurologic function in control animals made ischemic for similar durations but not given any drug. Based on this comparison an evaluation is made as to whether a drug prevents paraplegia or whether it decreases the number of animals that have any neurologic abnormality. For these two evaluations, the 3 grades of neurologic function are classified in 2 ways:

(1) Classification P - to determine if the drugs prevent paraplegia, grade 0 (paraplegic) animals are considered to have no response to treatment, and grade 1 plus grade 2 animals (any neurologic function) are considered to have positive responses;

(2) Classification A - to determine whether the drugs reduced the number of animals with any abnormal neurologic function, grade 0 and grade 1 animals are considered to have no response to treatment and grade 2 animals (normal) are regarded as having positive responses.

A quantal dose-response method can be adapted as described above to analyze the results. A computerized curve fitting process is used to fit S-shaped (logistic) curves to the fraction of animals showing no response to treatment as a function of the duration of ischemia. For each treatment group, the duration of ischemia required to produce both paraplegia (P classification) and loss of normal function (A classification) in 50% of the animals is computed. The $ET_{50}$ (effective time for 50% damage) for either paraplegia or neurologic abnormality measures the average duration of ischemia required to produce either type of neurologic deficit. Thus, the average length of ischemia required to produce loss of normal neurological function or complete paraplegia for any treatment group (and controls) can be determined.

All animals are made ischemic for predetermined durations (e.g., 15 to 60 min.) and then the occlusions are removed. The animals are 9graded at 2 hr after the end of ischemia, 18 hr after the insult and then on the fifth day after the ischemic injury. The durations of ischemia are selected to span the times required to produce all grades of damage from full recovery to permanent paraplegia. With any given treatment the appropriate durations of ischemia to try are not initially known However, after the first few rabbits are studied, the duration of ischemia in subsequent animals can be increased or decreased so that all grades of damage are included. Animals are maintained for at least 5 days after the ischemic insult. If any rabbit fails to live for the full 5 days, it is excluded from the study. Approximately 5% of the animals die after surgery and significant differences in deaths among control or treatment groups are not observed.

Specific serotonin antagonists were tested using the rabbit spinal chord ischemia model as follows.

Lysergic acid diethylamide (LSD) (National Institute of Drug Abuse), dissolved in isotonic saline and injected into rabbits at a dosage of 0.15 mg/kg 5 minutes after the onset of ischemia, significantly increases the $ET_{50}$ according to the P classification when evaluated at 2 hours after the end of ischemia. The effect of the single dose of LSD however, is not sustained. Many treated animals that are normal or paretic at 2 hours develop signs of new neurologic abnormality by 18 hours whereas relatively fewer controls develop further deficits. By 18 hours there is no significant difference between treatment and control groups. Furthermore, when data are rated according to the A classification, no significant effect of treatment is seen at any time. At the doses used, rabbits become tremulous and inordinately responsive to many stimuli for about 1.5 hours.

2-Bromolysergic acid diethylamide (BOL) (National Institute of Drug Abuse), dissolved in isotonic saline and injected into rabbits at a dosage of 1.5 mg/kg 5 minutes after the onset of ischemia, increases the $ET_{50}$ when compared to controls according to both the P and A classifications. The salutary effect of BOL is dose dependent, since $ET_{50}$ is further increased when BOL is administered at a dosage of 3.0 mg/kg. At a dosage of 3.0 mg/kg administered 5 minutes after onset of ischemia, the increase of $ET_{50}$ over controls in BOL treated rabbits is statistically significant. The benefits of BOL treatment are maintained during the 5 day post-treatment observation period; no significant further deficits are observed. A single bolus of BOL, administered intravenously 15 minutes before occlusion of the aorta, significantly improves the $ET_{50}$ (by the P classification) when rabbits are evaluated at 18 hours after insult. A 1.5 mg/kg dosage of BOL administered prophylactically 15 minutes prior to insult has a greater effect on $ET_{50}$ than the same dosage administered 5 minutes after the onset of ischemia. BOL at 3 mg/kg causes animals to become lethargic but arousable for about 10 minutes after which they return to normal. A 1.5 mg/kg dose has no obvious behavioral effects.

The protective effects of cinanserin (E.R. Squibb and Sons, Princeton, N.J.), whether given before or after the onset of ischemia, are almost identical to the effects of BOL. Cinanserin at 10 mg/kg causes a pattern of lethargy similar to the pattern observed after administration of BOL.

1.0 mg/kg of cyproheptadine (Merck, Sharp, and Dohme Research Lab., West Point, PA), dissolved in water and administered 10 to 15 minutes prior to the initiation of ischemia causes a significant increase in $ET_{50}$. The same dose administered 5 minutes after the onset of ischemia does not significantly alter the $ET_{50}$ over controls, but when the dose is increased to 2.0 mg/kg the ET is significantly improved. Animals do not show any grossly apparent behavioral abnormalities at these doses.

Methysergide (Sandoz Pharmaceuticals, E. Hanover, NJ), dissolved in isotonic saline and administered at a dose of 4.0 mg/kg 10 to 15 minutes prior to the onset of ischemia does not significantly increase the $ET_{50}$ when compared to the control. Because of low solubility it is not possible to test higher doses without markedly increasing the volume of solution. Animals do not show any behavioral effects from this dose of methysergide.

Administration of quipazine (Miles Labs.) or bufotenine (Sigma Chemical Co., St. Louis, MO) which are serotonin antagonists, does not increase neurologic damage in the rabbit chord ischemia model. However, administration of bufotenine in conjunction with cyproheptadine reverses the protective effect of cyproheptadine.

Use

The serotonin antagonists of the invention can be administered (e.g., intravenously intrathecally, orally, subcutaneously, or nasally or sublingually, transdermally, or using a slow release preparation) to a human patient who has suffered a stroke. The compounds are administered a short enough time after the onset of the stroke (preferably less than 20 minutes after onset), and in sufficient dosage to provide a concentration of the compound in the bloodstream or CNS which is effective to reduce neurological damage.

The serotonin antagonists of the invention can also be administered prophylactically to individuals who have been identified as high-risk patients for stroke. The compounds can be kept by the patient or the patient's physician in a readily accessible location, and, when it is determined that the patient is on the verge of stroke onset (e.g., the patient feels numbness or weakness in the extremities), the compound can be administered immediately. Since administration at this early stage will be expected to be more effective than administration following stroke onset the dosage required will be lower.

The compounds generally will be administered in combination with a pharmaceutically acceptable carrier substance, e.g. saline. The compounds can be administered in a dosage of 0.01 to 100 mg/kg, preferably 0.15 to 10.0 mg/kg.

Generally, the optimal dose for a given serotonin antagonist is about one-fourth of the $LD_{50}$, on a per-weight basis, of the serotonin antagonist in mammals. This dosage varies from compound to compound, depending on how powerful a given compound is. Generally, the compounds can be administered in a dosage of 0.01 to 100 mg/kg, preferably 0.15 to 10.0 mg/kg.

The precise mechanism of action of the compounds is not yet known, but it has been determined that the serotonin antagonists probably do not alter CNS blood flow during ischemia, indicating that these compounds probably function at the cellular level.

Other embodiments are within the following claims.

I claim:

1. A method of reducing stroke-induced neurological damage in a human patient comprising administering to the patient an effective amount of a pharmaceutically acceptable neurological-damage-reducing serotonin antagonist.

2. The method of claim 1 wherein said neurological-damage-reducing serotonin antagonist is administered no later than 24 hours following the onset of said stroke.

3. The method of claim 2 wherein said neurological-damage-reducing serotonin antagonist is administered no later than 1 hour following the onset of said stroke.

4. The method of claim 3 wherein said neurological-damage-reducing serotonin antagonist is administered no later than 20 minutes following the onset of said stroke.

5. The method of claim 1 wherein said neurological-damage-reducing serotonin antagonist is administered to said patient prior to the onset of said stroke such that at the time of the onset of said stroke there is a sufficient amount of said neurological-damage-reducing serotonin antagonist present in the bloodstream or CNS of the patient to reduce stroke-induced neurological damage.

6. The method of claim 1, wherein said neurological-damage-reducing serotonin antagonist comprises cinanserin.

7. The method of claim 1, wherein said neurological-damage-reducing serotonin antagonist is administered in combination with a pharmaceutically acceptable carrier substance.

8. The method of claim 1, wherein said neurological-damage-reducing serotonin antagonist is administered intravenously, intrathecally, orally, subcutaneously, or nasally.

* * * * *